United States Patent
Deak et al.

(10) Patent No.: US 9,721,415 B2
(45) Date of Patent: Aug. 1, 2017

(54) MAGNETIC HEAD FOR BANKNOTE DETECTION

(71) Applicant: MultiDimension Technology Co., Ltd., Zhangjiagang (CN)

(72) Inventors: James Geza Deak, Zhangjiagang (CN); Mingfeng Liu, Zhangjiagang (CN); Jianming Bai, Zhangjiagang (CN); Min Zhu, Zhangjiagang (CN)

(73) Assignee: MultiDimension Technology Co., Ltd., Zhangjiagang (CN)

( * ) Notice: Subject to any disclaimer, the term of this patent is extended or adjusted under 35 U.S.C. 154(b) by 60 days.

(21) Appl. No.: 14/439,981

(22) PCT Filed: Oct. 30, 2013

(86) PCT No.: PCT/CN2013/086245
§ 371 (c)(1),
(2) Date: Apr. 30, 2015

(87) PCT Pub. No.: WO2014/067462
PCT Pub. Date: May 8, 2014

(65) Prior Publication Data
US 2015/0294521 A1    Oct. 15, 2015

(30) Foreign Application Priority Data
Oct. 31, 2012    (CN) .......................... 2012 1 0424954

(51) Int. Cl.
*G01R 33/02*    (2006.01)
*G07D 7/04*    (2016.01)
(Continued)

(52) U.S. Cl.
CPC .............. *G07D 7/04* (2013.01); *G01N 27/90* (2013.01); *G01R 15/20* (2013.01);
(Continued)

(58) Field of Classification Search
CPC .. B64G 1/366; G01R 33/0206; G01R 33/028; G01R 33/038; G01R 33/1215;
(Continued)

(56) References Cited

U.S. PATENT DOCUMENTS

| 2006/0102721 A1* | 5/2006 | Goetz | ................... G01D 3/032 235/440 |
| 2006/0110023 A1* | 5/2006 | Goetz | ................... G06K 9/186 382/139 |

(Continued)

FOREIGN PATENT DOCUMENTS

| CN | 102722932 A | 10/2012 |
| CN | 202694446 U | 1/2013 |

(Continued)

OTHER PUBLICATIONS

CN 102722932 Machine Translation; Oct. 10, 2012.*
(Continued)

*Primary Examiner* — Huy Q Phan
*Assistant Examiner* — Raul Rios Russo
(74) *Attorney, Agent, or Firm* — Schwegman Lundberg & Woessner, P.A.

(57) ABSTRACT

A magnetic currency verification head may include a magnetoresistive sensor chip, and a magnetic bias unit disposed on the side of the magnetoresistive sensor chip away from the detection surface of the magnetic currency verification head, and separated from the magnetoresistive sensor chip; the magnetoresistive sensor chip comprises a gradiometric bridge circuit that includes magnetic sensor elements; the sensitive direction of the magnetic sensor elements is parallel to the detection surface of the magnetic currency verification head; and the magnetic bias unit has a recessed magnetic structure configured such that the magnetic field generated by the magnetic bias unit only has a small
(Continued)

magnetic field component in the direction parallel to the detection surface, thereby enabling the magnetic sensor elements to operate in their linear range. As a result, the magnetic currency verification head has high sensitivity and signal-to-noise ratio.

15 Claims, 9 Drawing Sheets

(51) Int. Cl.
*G01R 33/028* (2006.01)
*G01N 27/90* (2006.01)
*G01R 33/38* (2006.01)
*G01R 15/20* (2006.01)
*G01R 33/09* (2006.01)
*G11C 19/08* (2006.01)

(52) U.S. Cl.
CPC ......... *G01R 33/0283* (2013.01); *G01R 33/09* (2013.01); *G01R 33/091* (2013.01); *G01R 33/38* (2013.01); *G11C 19/085* (2013.01)

(58) Field of Classification Search
CPC .... G01R 15/20; G01R 33/0283; G01R 33/38; G01N 27/90; G11C 19/085; H01F 7/0273
USPC ....... 324/51, 55, 200, 207.21, 227, 228, 252
See application file for complete search history.

(56) References Cited

U.S. PATENT DOCUMENTS

| 2007/0209904 A1* | 9/2007 | Freeman | G07D 7/04 194/210 |
| 2009/0152356 A1* | 6/2009 | Reddy | G06K 9/186 235/449 |
| 2013/0127457 A1* | 5/2013 | Musha | B82Y 25/00 324/252 |
| 2014/0035570 A1* | 2/2014 | Jin | G01R 33/098 324/252 |

FOREIGN PATENT DOCUMENTS

| CN | 102968845 A | 3/2013 |
| CN | 202916902 U | 5/2013 |
| CN | 203038357 U | 7/2013 |
| DE | 102010035469 A1 | 3/2012 |
| JP | 04-013925 A | 1/1992 |
| JP | 2012-47685 A | 3/2012 |
| WO | WO-2014/067462 | 5/2014 |

OTHER PUBLICATIONS

DE 102004063539 Machine Translation; Sep. 29, 2005.*
JP H0413925 Machine Translation; Jan. 17, 1992.*
DE 102010035469 Machine Translation; Mar. 1, 2012.*
"International Application No. PCT/CN2013/086245, International Search Report and Written Opinion [with English translation] mailed Jan. 30, 2014", (Jan. 30, 2014), 22 pgs.

* cited by examiner

MAGNETIC HEAD FOR BANKNOTE DETECTION

PRIORITY CLAIM TO RELATED APPLICATIONS

This application is a U.S. national stage application filed under 35 U.S.C. §371 from International Application Serial No. PCT/CN2013/086245, which was filed 30 Oct. 2013, and published as WO 2014/067462 on 8 May 2014, and which claims priority to Chinese Application No. 201210424954.6, filed 31 Oct. 2012, which applications and publication are incorporated by reference as if reproduced herein and made a part hereof in their entirety, and the benefit of priority of each of which is claimed herein.

TECHNICAL FIELD

This document relates to a magnetoresistive sensor technology and more particularly to magnetic currency verification heads.

BACKGROUND

Currency verification heads are commonly used in daily life in applications such as vending machines, bank note counting, and counterfeit detection. Typically, banknotes use magnetic ink and other magnetic security features that produce a very weak magnetic signal. Therefore, the sensor used in a currency verification head needs to have high sensitivity, low noise, and high signal to noise ratio.

Figure 1:
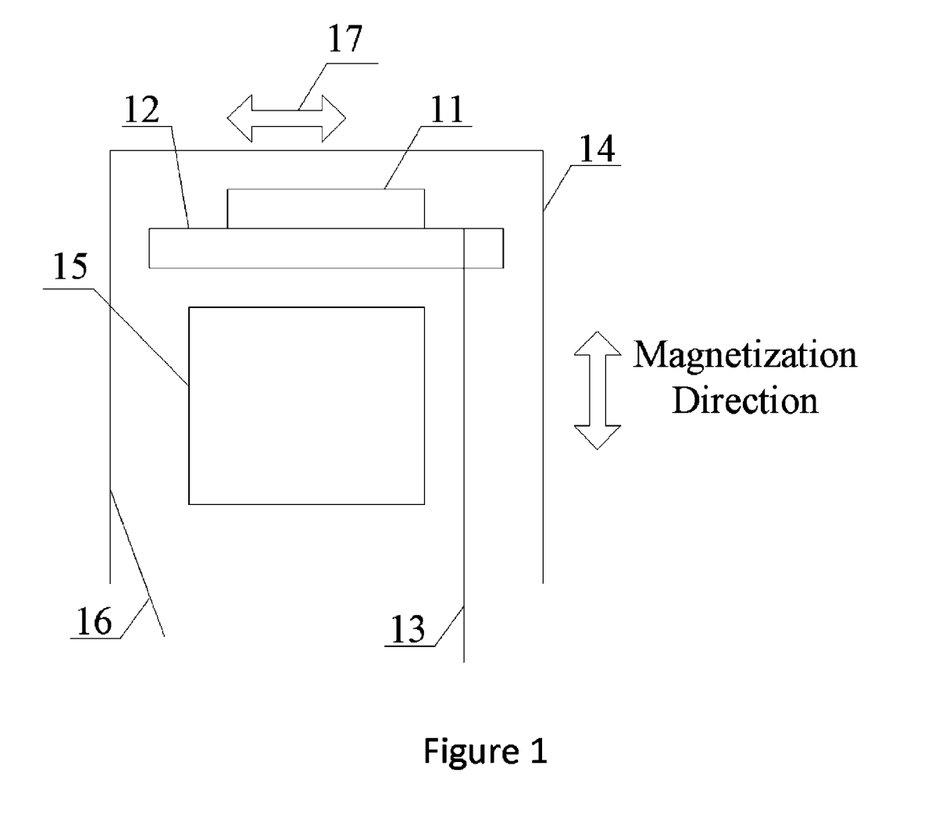
FIG. 1 shows a prior art style implementation of a magnetic currency verification head that is described in case 1.

FIG. 1 shows existing currency verification head technology, which detects the perpendicular component of the magnetic field, produced by the magnetic ink on the paper currency. Typically, the material used is indium-antimonide (InSb). This type of sensor has the following disadvantages:

(1) Low sensitivity and low signal-to-noise ratio;

(2) InSb Hall Effect sensors are strongly dependent on temperature, thereby requiring complex circuitry to compensate;

(3) The magnetic biasing device must be selected to produce sufficient magnetic field in order to generate a signal with magnitude that is larger than the noise inherent in the sensor, in order to overcome the signal-to-noise limitations of the Hall effect sensor. Thus, when using Hall Effect sensors magnetic currency verification head tend to be large;

(4) A magnetic field produced by a monolithic magnetic biasing device with one pole on a flat front surface has an in-plane component that makes detection of the field produced by the paper currency difficult.

Therefore, a need exists to develop a currency verification head to accurately measure this field produced by the paper currency.

SUMMARY

The present subject matter provides a magnetic currency verification head that can use magnetoresistive sensors that detect the in-plane components of the field produced by the media. These sensors are preferably tunneling magnetoresistive sensors, but may also include giant magnetoresistance sensors, or anisotropic magnetoresistance sensors.

The magnetic currency verification head may comprise a magnetoresistive sensor chip, wherein said magnetoresistive sensor chip includes a gradiometric bridge circuit wherein bridge arms are magnetic sensor elements, and the sensitive direction of the magnetic sensor elements is parallel to the magnetic currency verification head detection surface.

The magnetoresistive sensor chip is may be located away from the magnetic currency verification head detection surface and placed separately from a magnetic bias unit. The magnetic biasing unit may have a recessed structure, and the recessed structure may be arranged such that the magnetic bias field generated by the magnetic bias unit in the direction parallel to the magnetic currency verification head detection surface is small such that the magnetic sensing elements operate in their linear regime.

Preferably the magnetic bias unit further comprises a permanent magnet and the side of the permanent magnet facing the magnetoresistive sensor chip has a recess.

Preferably, the magnetic bias unit is a rectangular permanent magnet, wherein said rectangular permanent magnet includes recessed grooves or pits cut perpendicular to magnetic currency verification head detection surface on the side facing the magnetoresistive sensor chip.

Preferably, the magnetic bias unit comprises a rectangular permanent magnet and pole piece composed of high permeability magnetic material, and the pole piece surface has a recessed rectangular cavity.

Preferably, the magnetic bias unit comprises a rectangular permanent magnet and a rectangular-ring-shaped pole-piece composed of high permeability magnetic material.

Preferably, the magnetic bias unit comprises two separately disposed rectangular permanent magnets.

Additionally, a non-magnetic material or a soft ferromagnetic material is placed between the two rectangular permanent magnets.

Preferably, the magnetic field generated by the magnetic bias unit in a direction parallel to the sensing direction of the magnetic sensor elements is less than 25 gauss.

Preferably, the magnetic sensor elements are tunneling magnetoresistive (TMR) elements, giant magnetoresistive (GMR) elements, or anisotropic magnetoresistive (AMR) elements.

Preferably, said TMR, GMR, or AMR magnetic sensor elements are connected in series, parallel, or a combination of series and parallel.

Preferably, the magnetic currency verification head further comprises a metal casing to enclose the magnetoresistive sensor chip and the magnetic bias unit, wherein said metal casing has an opening on the side opposite to the magnetic currency verification head detection surface.

Preferably, the magnetic currency verification head further comprises a metal casing to enclose the magnetoresistive sensor chip and the magnetic bias unit, wherein said metal housing is provided with a ground terminal.

Preferably, the metal casing is filled with an injection molded material to secure the components.

The present subject matter has the following beneficial effects:

(1) The magnetic currency verification head of the present invention is suitable for detection of currency containing hard or soft ferromagnetic materials;

(2) The magnetic currency verification head of the present invention includes TMR, GMR, or AMR elements as the magnetoresistive sensor, and compared with an InSb Hall element, will have higher sensitivity and higher signal to noise ratio, yielding a magnetic currency verification head with higher sensitivity and higher signal to noise ratio.

(3) the magnetoresistive element production process is relatively simple, and the materials are less susceptible to the effects of temperature and stress, and can be fabricated with high yield, such that the magnetic currency verification head production process is relatively simple and low cost;

(4) The use of a magnetic bias unit with a concave recess, causes the magnetic field component in the direction parallel to the sensing direction of the magnetoresistive sensor elements is small or zero, enabling the magnetic sensor to operate in its linear range, guaranteeing the magnetic currency verification head operates optimally;

(5) Because the magnetic currency verification head sensor chip incorporates a gradiometric sensor bridge circuit; the magnetic currency verification head is insensitive to common mode magnetic field or external magnetic interference;

(7) The resulting magnetic currency verification head can be used for counterfeit detection and also in a cash register type device;

(8) The disclosed magnetic currency verification head uses a flexible printed circuit board to connect the PCB to the output pins, said flexible circuit board will not restrict the shape of the permanent magnet, and it is thus helpful to the design of permanent magnet.

FIGURES

FIG. 2 (A) shows a drawing of the magnetic field distribution for the rectangular permanent magnet illustrated in FIG. 1.

FIG. 2 (B) illustrates the magnetic field components at the detection surface of the magnetic currency verification head illustrated in FIG. 1.

FIG. 3 (A) shows a drawing of the magnetic field distribution for the rectangular permanent magnet described in case 2.

FIG. 3 (B) illustrates the magnetic field components at the detection surface of the magnetic currency verification head described in case 2.

FIG. 6 (A) shows the magnetic field distribution for a preferred embodiment.

FIG. 6 (B) illustrates the magnetic field components at the detection surface of the magnetic currency verification head for a preferred embodiment FIG. 7 (A) shows the magnetic field distribution around the magnetic bias unit of a preferred second embodiment.

FIG. 7 (B) illustrates the magnetic field components at the detection surface of the magnetic currency verification head for a preferred second embodiment.

FIG. 7 (C) shows a perspective view of the magnetic pole-piece used in a preferred second embodiment.

FIG. 8 (A) shows the magnetic field distribution around the magnetic bias unit of a third preferred embodiment.

FIG. 8 (B) illustrates the magnetic field components at the detection surface of the magnetic currency verification head for a third preferred embodiment.

FIG. 8 (C) shows a perspective view of the magnetic pole-piece used in a preferred third embodiment.

FIG. 9 (A) shows the magnetic field distribution around the magnetic bias unit of a fourth preferred embodiment.

FIG. 9 (B) illustrates the magnetic field components at the detection surface of the magnetic currency verification head for a fourth preferred embodiment.

DESCRIPTION

The embodiments described below in conjunction with the accompanying drawings, present detailed implementations of the present subject matter. In a particular embodiment, like reference numerals identify similar features or elements.

Prior Art Example 1

FIG. 1 shows a first example drawing of the magnetic currency verification head. The magnetic currency verification head includes a sensor chip 11, printed circuit board (PCB) 12, input/output pins 13, metal case 14, permanent magnet 15, and injection molding inside the metal shell body (not shown in the figure). Metal casing 14 has an opening on the opposite side from the testing surface, used for assembly and input/output connection pins. The magnetoresistive sensor chip 11 is located near the part of the metal case 14 that comprises the detection surface; the magnetic susceptibility perpendicular to the detection surface is small. Sensor chip 11 and permanent magnet 15 is located on opposite sides of the PCB 12, respectively. The permanent magnet 15 magnetization direction is as shown on the right side of FIG. 1. The PCB 12 does not need to be in direct contact with permanent magnet 15. The input and output of sensor chip 11 respectively are connected with the corresponding terminal on the PCB 12, the PCB 12 can support sensor chip 11. Input and output pins 13 are electrically connected to PCB 12, in such a manner as to connect the input and output pins 13 to the corresponding input and output connections of the magnetoresistive sensor chip 11. The other end of the input and output pins 13 serve as the interface of the magnetic currency verification head. Using an InSb Hall element sensor chip 11, the sensitive direction is perpendicular to the detection surface 17 of the magnetic currency verification head. Metal casing 14 has a grounding pin 16. The grounding pin 16 and metal casing 14 are used for shielding electromagnetic interference from outside of metal case 14, and protect against electrostatic discharge. The shape of a permanent magnet 15 can be a rectangle. The injection mold has size and shape that permits it to fit within the metal casing 14, along with the PCB 12 and matching the shape and size of the permanent magnet 15 for fixing them within the metal casing 14, additionally the injection mold provides electrical isolation between the permanent magnet 15 and the PCB 12.

When the magnetic currency verification head illustrated in Example 1 uses an InSb Hall effect sensor chip, the magnetic currency verification head has low sensitivity and poor SNR. Because the production process for InSb Hall elements is complex, and they are subject to the effects of temperature and stress, the production process yield is low, resulting in an overly complex and costly magnetic currency verification head. An additional complication is because the output pins are directly connected to the PCB, and the output lead pins cannot directly pass through the permanent magnet, the position of the output pins limits the size of the permanent magnet, increased design difficulty. Further, since the permanent magnet used in magnetic currency verification head comparative Example 1 is rectangular, when using a TMR sensor chip, a rectangular permanent magnet produces a large magnetic field component along the sensitive direction of the MTJ element, causing the MTJ element to deviate from its linear response region, and it may even drive the MTJ element into saturation, thus affecting the performance of magnetic currency verification head, and possibly even leading to a magnetic currency verification head that cannot function.

The distribution of fields produced by a rectangular magnet of the type in the prior art currency verification head is shown in detail in FIG. 2(A). Here, a permanent magnet 15 with rectangular cross-section is magnetized in a direction perpendicular to the sensing surface 40 denoted by line AA. The magnetic sensor 41 is situated below the sensing surface 40 along the line denoted as BB. The permanent magnet 15 produces a magnetic field described by contours of constant B field 23. FIG. 2(B) shows the B field 23 components of the lines that are tangential 28 and normal 27 to the sensing surface. The horizontal axis of the plot 29 denotes the distance along the sensing surface along line AA. In a conventional currency verification head utilizing a Hall sensor only the normal component 27 produces a signal, so the tangential component 28 of the B field does not induce a signal, so the existence of a large tangential B field does not degrade the performance of the currency verification head.

If the magnetic sensor sensing detects magnetic field in direction parallel to the surface of 40, the biasing magnet design must be improved, with the aim of reducing parallel field component caused by permanent magnet in the vicinity of the magnetic field sensor.

Prior Art Example 2

Figure 2:
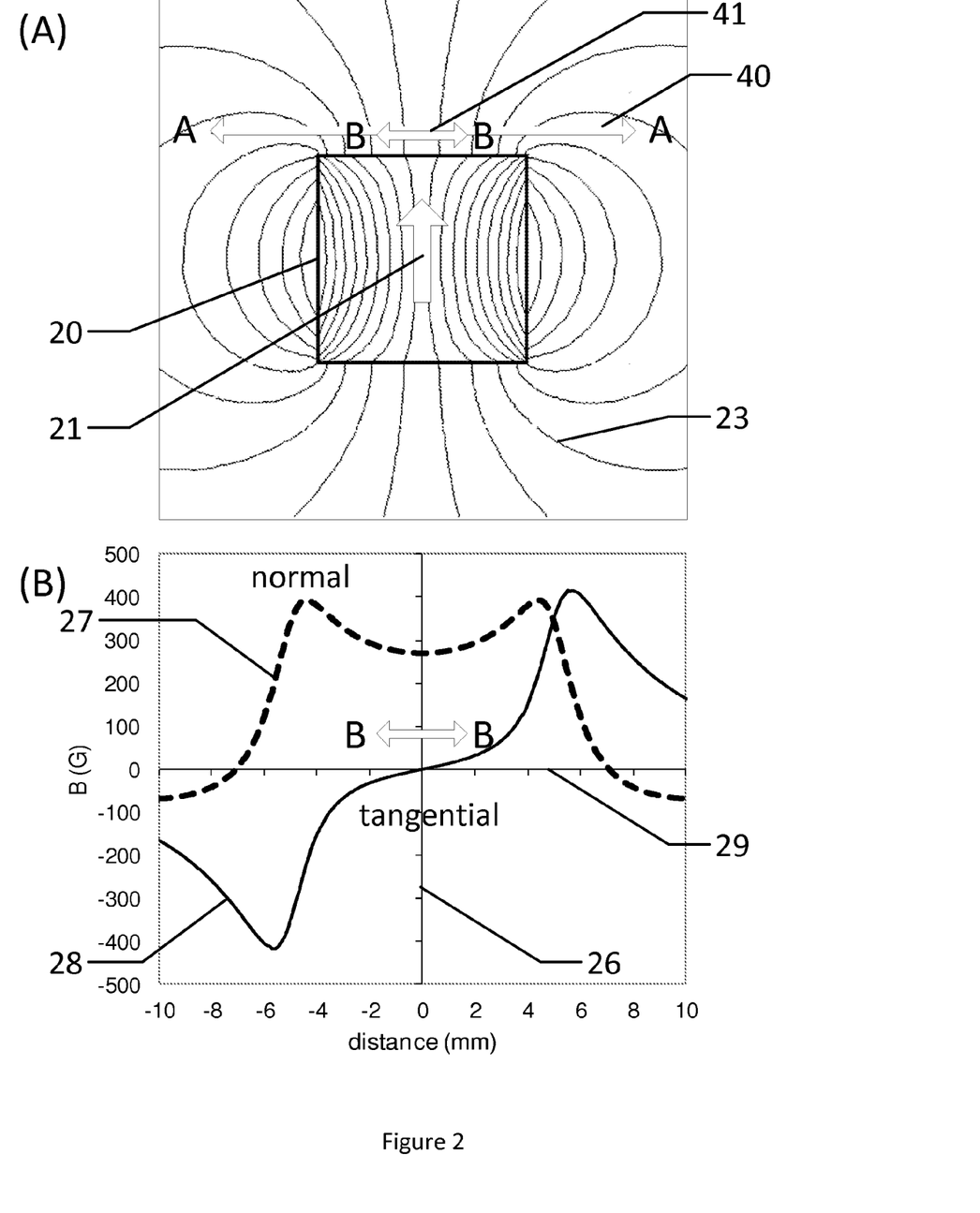
Figure 3:
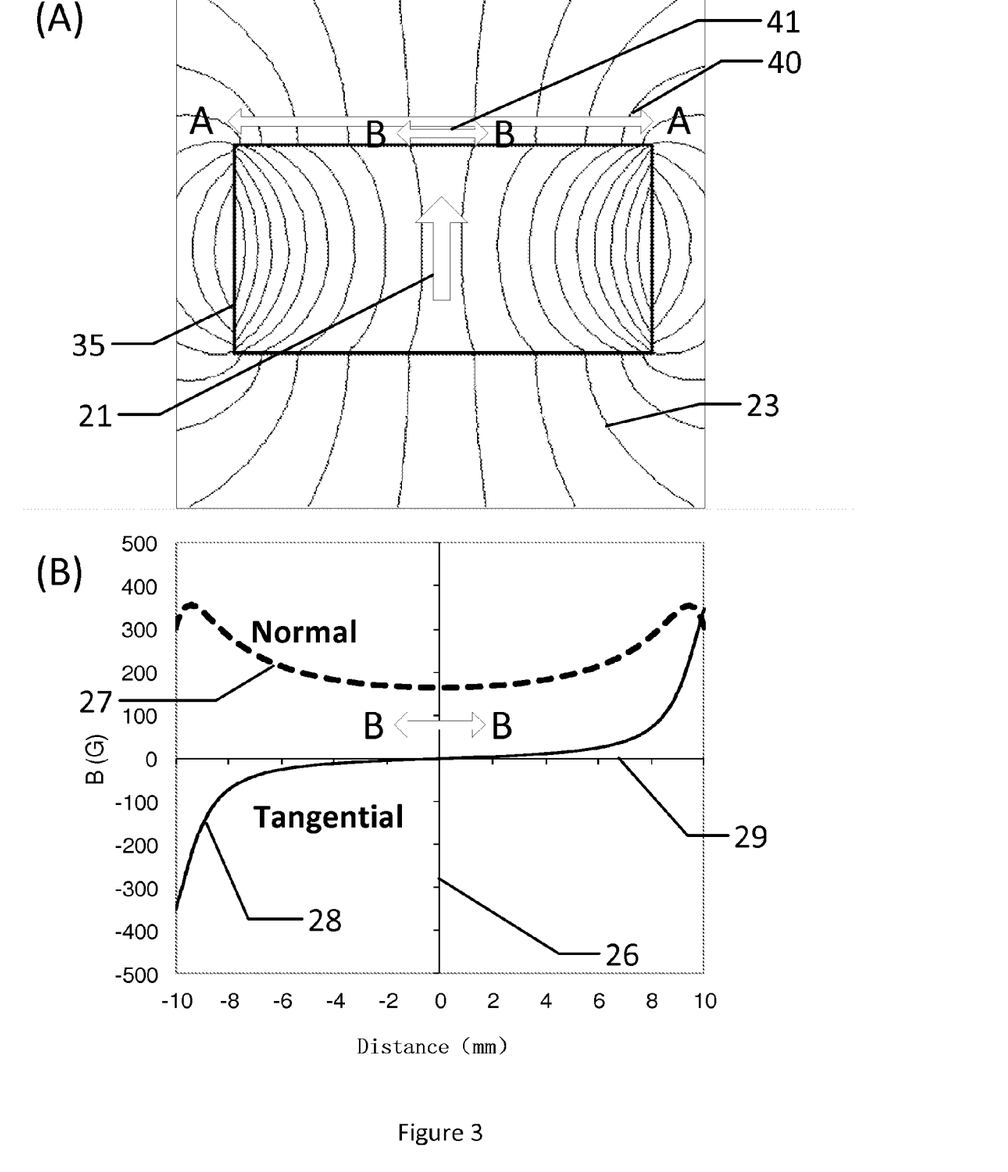

An effective method to solve these problems would be to increase the biasing magnet size relative to the sensing element. FIGS. 3 (A) and 3 (B) illustrate the magnetic field distribution and magnetic field intensity distribution of a second example prior art design rectangular permanent magnet. From comparison of FIG. 3 (A) and FIG. 2 (A) it can be seen that biasing magnet 35 is significantly larger than adjacent sensor element 41. As shown in FIG. 3(A), the permanent magnet 35 is magnetized 21 in a direction perpendicular to the sensing surface 40 denoted by line AA. The magnetic sensor chip 41 is situated below the sensing surface 40 along the line denoted as BB 41. The permanent magnet 35 produces a magnetic field described by B field contours 23. FIG. 3(B) shows the B field 23 that are tangential 28 and normal 27 to the sensing surface. The horizontal axis of the plot 29 denotes the distance along the sensing surface along line AA. Compared with the previous example, the parallel component of the magnetic field 28 is obviously smaller.

Unfortunately there is a problem with case 2, and that is the size of the magnetic currency verification head is larger, which increases difficulty in building the head into a system. Additionally, the larger permanent magnet and magnetic currency head increases product cost.

Embodiment of the Present Subject Matter

Figure 4:
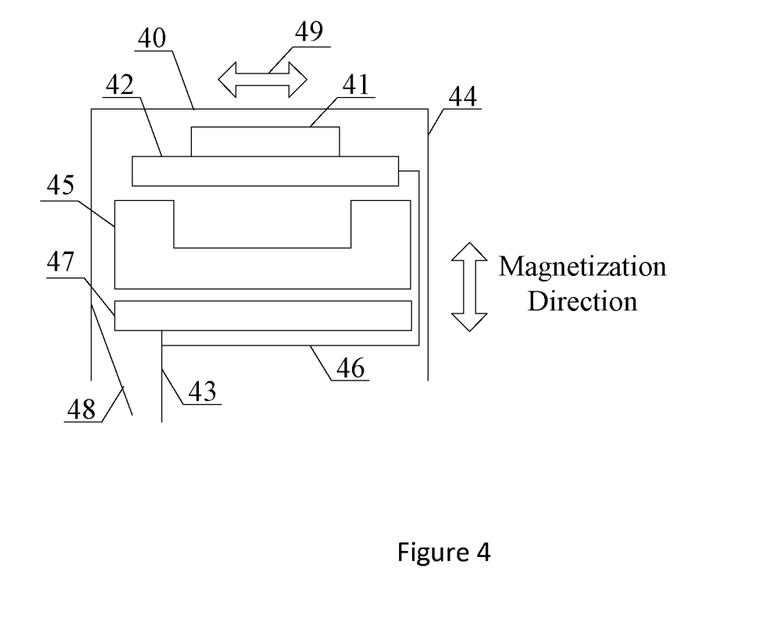
FIG. 4 is a schematic view of the magnetic currency verification head according to an embodiment.

FIG. 4 shows a schematic view of a possible embodiment of the magnetic currency head. This specific embodiment includes a magnetoresistive sensor chip 41, a printed circuit board 42, output lead pin 43, a metal shell 44, the groove-shaped magnetic biasing device 45, a flexible printed circuit board (FPC) 46, the first an injection mold 47 and the second injection mold 50, installed beneath the detection surface 40. The magnetic bias unit is formed with a recess in the side of the unit, for example, a rectangular permanent magnet having rectangular grooves, or pits on one side. Metal casing 44 is composed of a nonmagnetic wear-resistant material, and has an opening in its side remote from the detection surface 40. Magnetoresistive sensor chip 41 is mounted in a metal housing 44 close to the detection surface 40. The distance between the outer detection surface of the housing 40 and the magnetoresistive sensor chip is less than or equal to 0.2 mm. The magnetoresistive sensor chip 41 and the magnetic bias unit 45 are located on opposite sides of the PCB 42, and the recessed portion magnetic bias unit 45 points towards the PCB 42. The magnetization direction of the magnetic bias unit 45 is perpendicular to the detection surface 40, as shown in FIG. 4. The second injection molded body 50 is located between the PCB 42 and the magnetic bias unit 45, in order to isolate the PCB 42 from the magnetic bias unit 45. Sensor chip 41 input terminal and the output terminal are respectively connected, for example with the corresponding terminals on the PCB 42, such that the PCB 42 is capable of rigidly supporting the sensor chip 41. The first injection mold 47 is opposite to the side of the magnetic bias unit 45 that has a concave recess. Input and output lead pins 43 are fixed in and pass through the first molded body 47. One end of the FPC 46 is connected with the PCB 42 corresponding electrical terminals, and the other end of the FPC 46 is electrically connected with the input and output pins 43, so that the input and output pins 43 provide an interface with the magnetoresistive sensor chip 41. The other end of the input/output pins 43 serve as the terminals of the magnetic currency verification head. The magnetoresistive sensor chip 41 includes at least one bridge circuit, the bridge circuit comprising at least one bridge arm, preferably each leg may comprise at least one element such as a tunneling magnetoresistive TMR, giant magnetoresistance GMR element or anisotropic magnetoresistance AMR element. Preferably, said TMR, GMR, or AMR magnetic sensor elements are connected in series, parallel, or a combination of series and parallel. In the present embodiment, the magnetoresistive sensor chip 41 has a full bridge configuration, wherein each arm comprises at least one magnetic sensing element. The sensitive direction of the magnetic component of the magnetic currency verification head 49 and is parallel to the detection surface, and the sensitive direction of the magnetic sensing element 49 is perpendicular to the direction of the magnetic recess in the magnetic bias unit 45. Preferably, the metal casing 44 is provided on the grounding lead pin 48, such that a grounded metal enclosure shields electromagnetic interference from outside the metal housing 44, and eliminates ESD problems. The second molded body 50 fits into the metal casing 44, between the PCB 42 and magnetic bias unit 45, rigidly fixing the PCB 42 and magnetic bias unit 45 inside the metal housing 44. Preferably, the first injection molded body 47 and the second injection molded body 50 can be snap fit.

Figure 5:
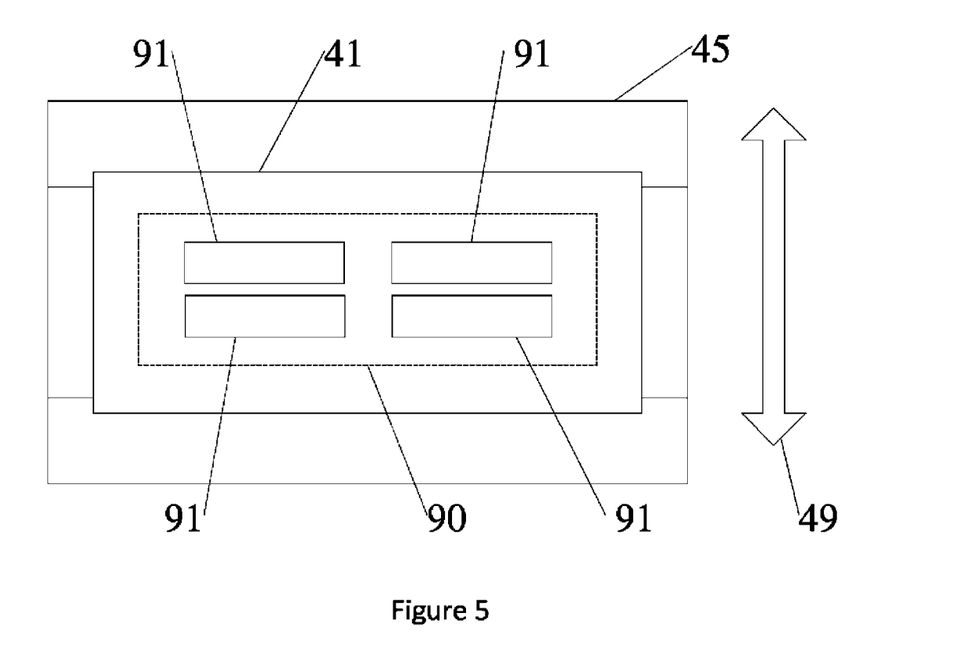
FIG. 5 shows a top-down view of a sensor ship used in an embodiment.

FIG. 5 shows a schematic top view of a full-bridge magnetoresistive sensor chip for a preferred implementation of a magnetic currency verification head. As shown, the magnetoresistive sensor chip 41 is located above the recessed side of the magnetic bias unit 45. In this region 90, the component of the magnetic field produced by the permanent magnet 45 parallel to the magnetoresistive sensor chip 41, the permanent magnet 45 generates less than 25 Gauss, within this region the magnetic bias unit 45 the magnetic flux density at the detection surface 40 will not saturate the magnetic sensor element 91. Therefore, we can ensure that within the detection area a magnetic element will operate in its linear region. In a direction parallel to the sensitive direction of the magnetic sensing element 49, the size range of the sense region 90 is roughly 1 mm to 10 mm.

When using the magnetic currency verification head, the paper currency moves over the detection surface. As a result, the magnetoresistive sensor chip detects the magnetic features of the paper currency creating a signal at the output pins, enabling magnetic identification of the currency.

Magnetic currency verification heads implemented according to a preferred embodiment may be used for identifying banknote identification marks composed of hard or soft magnetic material. For a magnetic currency verification head, it is preferable to sense the magnetic field in the direction parallel to the magnetic currency head detection surface, as such, TMR GMR or AMR sensing elements are preferred. Compared with an InSb Hall element, higher sensitivity and SNR of these magnetoresistive components permits realization of magnetic currency verification heads with higher sensitivity and signal to noise ratio. These magnetic components are relatively simple to fabricate, with low susceptibility to the effects of temperature and stress, resulting in high yield; as a result the magnetoresistive magnetic currency verification head fabrication process is relatively simple and low cost. Because the magnetoresistive magnetic currency verification heads use an FPC to interconnect the PCB and output pins, the shape of the flexible circuit board does not restrict the shape of the permanent magnets, and this simplifies the design of the permanent magnet. Because the permanent magnet of the magnetic currency verification head has a concave structure, the magnetic field of the permanent magnet at the vicinity of the magnetoresistive and along their sensing direction is very small or close to zero, so that the magnetoresistive elements operate in their linear region, thereby ensuring that the magnetoresistive magnetic currency verification head can operate optimally. The magnetoresistive magnetic currency verification head uses a magnetoresistive sensor chip comprised of magnetic elements in a gradiometer bridge circuit configuration, effectively suppressing the common-mode magnetic field interference from paper resulting from electromagnetic signals emanating from outside the magnetic currency verification head. The magnetoresistive head can be used in a paper money detector, but it can also be used in a point of sale system.

There are several means for implementing the magnetic bias unit 45; it can be a permanent magnet with a recess structure as described above, or permanent magnets plus pole-pieces, or a combination of several rectangular permanent magnets. These magnetic bias unit structures are advantageous they are easy to and low cost. Several examples of preferred implementations of magnetic bias units are described below.

Example 1

Figure 6:
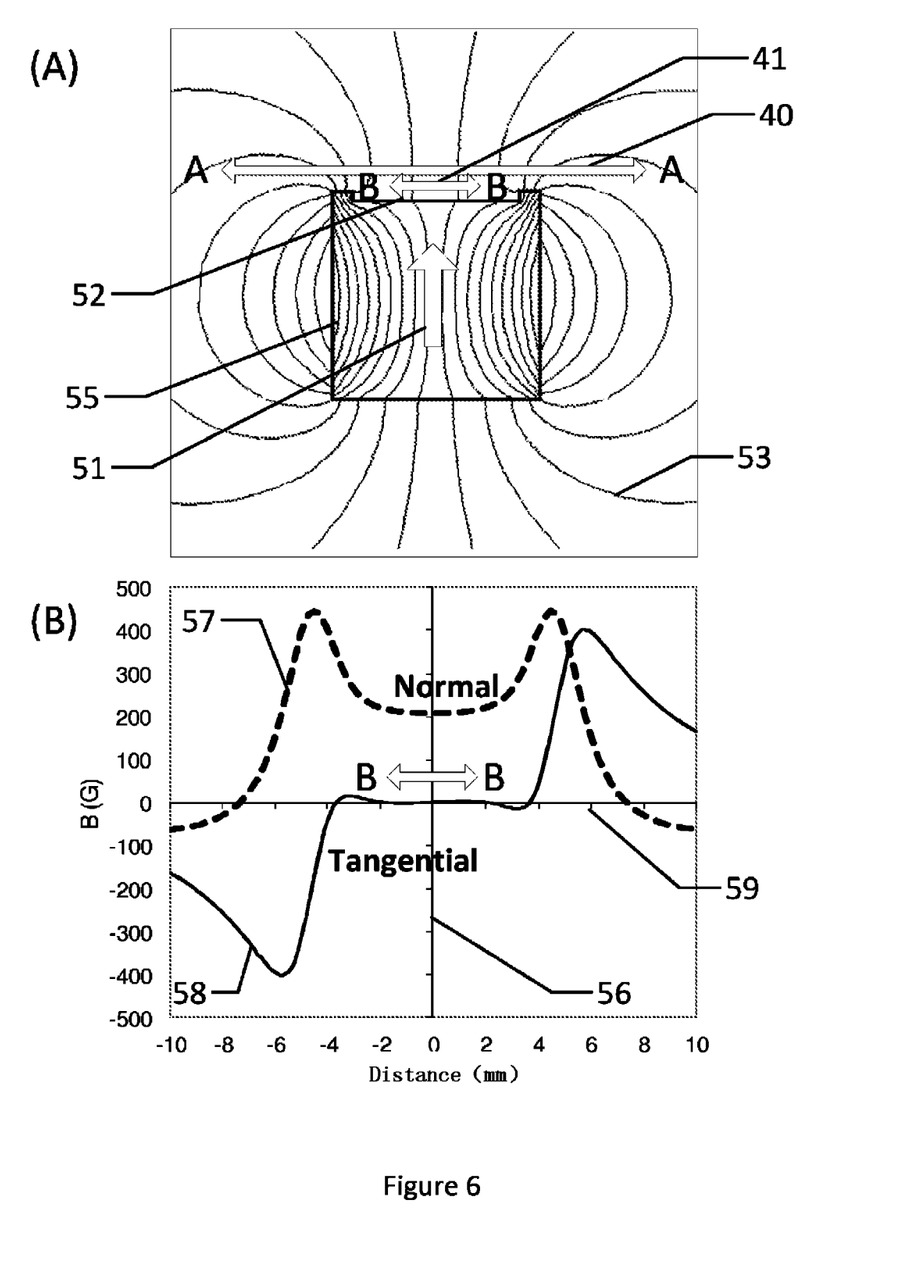

FIG. 6 (A) shows the distribution of the magnetic field according to Example 1 for a recessed rectangular permanent magnet. FIG. 6 (A), the permanent magnet 55 includes a slot cut into the surface closest to the detection surface 40. The slot is cut in a direction perpendicular to the surface of the permanent magnet 55. The magnetization 51 of the permanent magnet 55 is set perpendicular to the detection surface 40. In the center of the detection surface 40, the magnetic field 53 resulting from the influence of groove 52 is perpendicular to the detection surface 40, thus eliminating the horizontal magnetic field component in the vicinity of a magnetoresistive sensor chip, such as a TMR element 41.

FIG. 6 (B) shows a magnetic field intensity along the sensing surface 40 in the figure, wherein the dashed line 57 is the vertical component of the magnetic field intensity at the detection surface 40, the thin solid line 58 is parallel to the detection surface of the magnetic field strength component 40, the vertical axis 56 is magnetic field strength, and the horizontal axis is the distance from the center of the detection surface 40. As can be seen from the figure, the parallel component of the magnetic field strength 55 is small in the portion of the detection surface 40 over top of the slot, and the value of the magnetic field in this direction is significantly less than the prior art designs illustrated in FIG. 2 and FIG. 3.

It should be appreciated, there are other ways to achieve the purpose this slotted feature including through the use of pits.

Example 2

Figure 7:
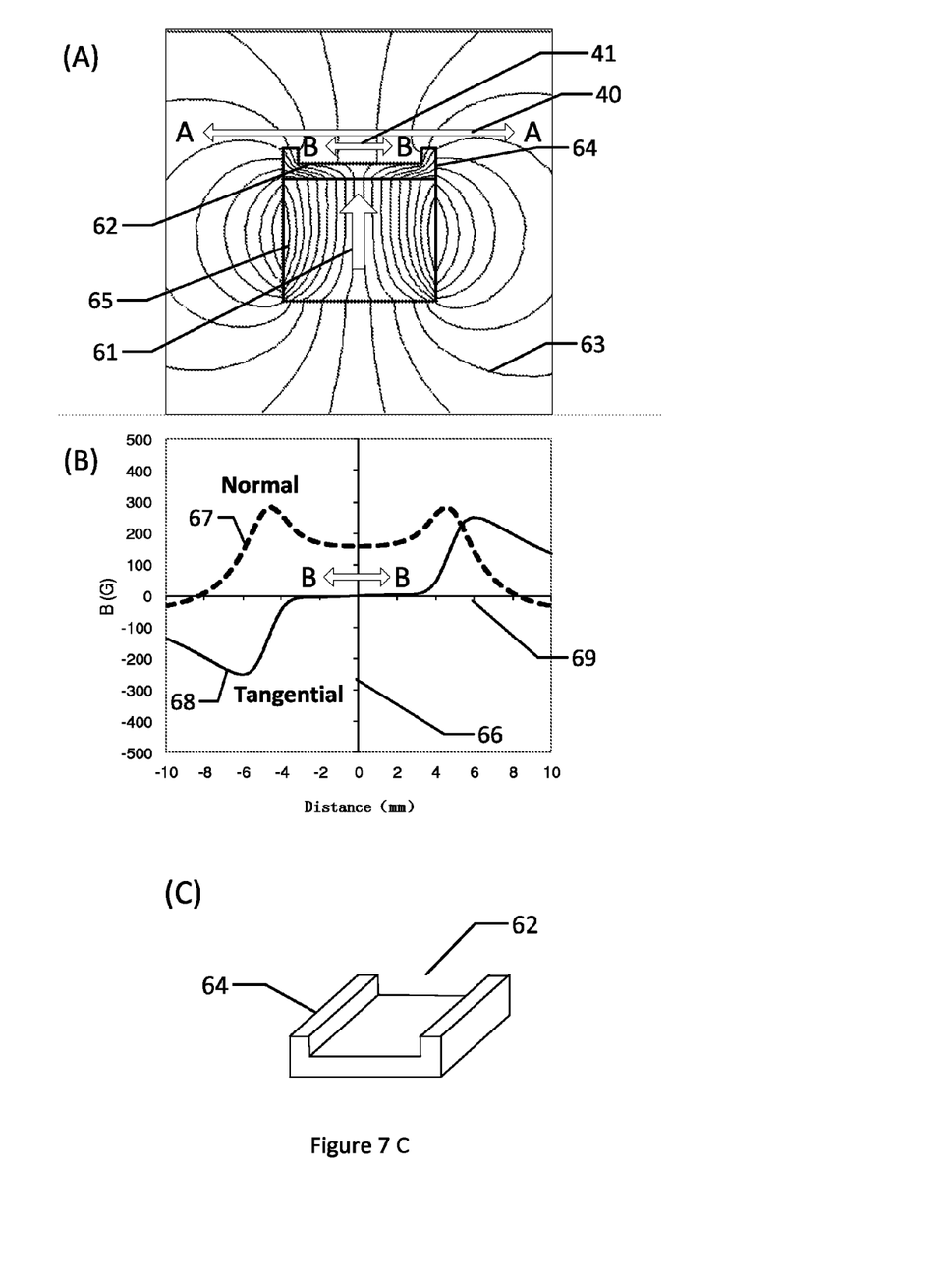

FIG. 7 (A) shows the distribution of the magnetic field lines for the magnetic currency verification head of Example 2. FIG. 7 (A), shows a permanent magnet 65 having a rectangular cross section with a top cover composed of soft ferromagnetic alloy sheet, also referred to as "pole pieces" 64, used to adjust the magnetic field component parallel to the detection surface 40. Pole piece 64 is usually made of a soft ferromagnetic alloy, such as permalloy. The magnetization direction 61 of the permanent magnet 65 is perpendicular to the detection surface 40, and the magnetization direction of the pole pieces 64 which determines the magnetic field distribution at the detection surface is determined by the magnetization direction of the permanent magnet. Recessed slot 62 in the pole piece serves to reduce the magnetic field in a direction parallel to the detection surface 40.

FIG. 7 (B) illustrates the magnetic field components along the detection surface 40 for the implementation described in example 2, wherein the dashed line 67 shows the magnetic field component perpendicular to the detection surface 40, the thin solid line 68 is shows the magnetic field component parallel to the detection surface 40, the vertical axis 66 is the magnetic flux density, and the horizontal axis represents the offset distance 40 from the center of the detection surface. As can be seen from the figure, the magnetic field strength parallel to the detection surface 40 is small in the region above the slot in the pole piece 64, and the value of the parallel component of the magnetic field is significantly less than that illustrated in the prior art cases shown in FIGS. 2 and 3.

FIG. 6 (C) is a perspective view of the pole pieces 64 described in example 2, wherein the groove structure 62 can be realized by casting, stamping, cutting and other methods.

Example 3

Figure 8:
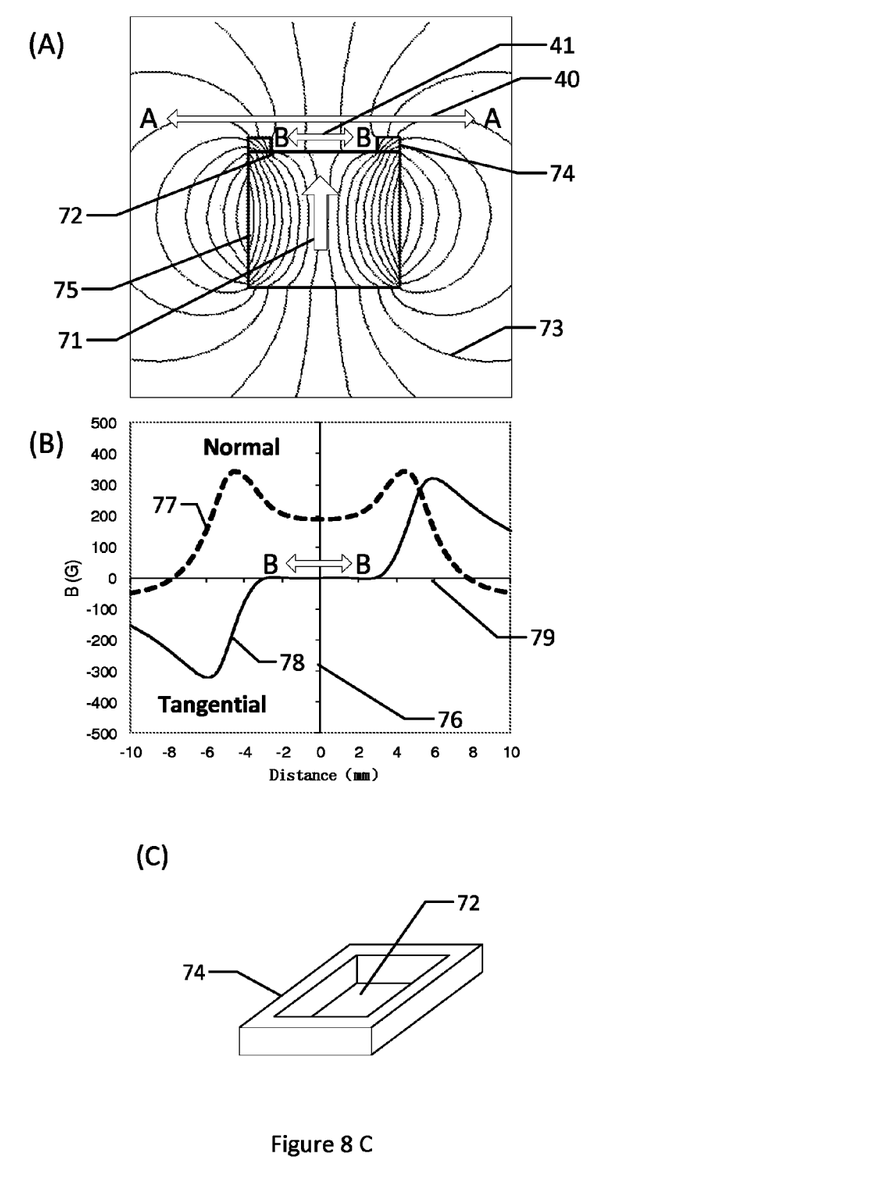

FIG. 8 (A) shows third example of the distribution of magnetic field produced by a magnetic bias unit. FIG. 8 (A) shows rectangular permanent magnet 75 covered by a soft ferromagnetic sheet, also referred to as a pole piece 74, used to adjust the magnetic field in the direction parallel to the detection surface 40 produced by the permanent magnet. Pole piece 74 is usually made of a soft magnetic alloy, such as permalloy. The magnetization direction 71 of the permanent magnet 75 is perpendicular to the detection surface 40, and the magnetization direction of the pole pieces 74 which determines the magnetic field distribution at the detection surface is determined by the magnetization direction of the permanent magnet 75. The opening 72 in the pole piece 74 serves to reduce the magnetic field parallel to detection surface 40.

FIG. 8 (B) shows the magnetic field distribution along the sensing surface 40 in the figure, wherein the dashed line 77 is the vertical component of the magnetic field on the detection surface 40, the thin solid line 78 is the parallel component of the magnetic field on detection surface 40, the vertical axis 76 is magnetic induction, and the horizontal axis is the distance from the center of the detection surface 40. As can be seen from the figure, the magnetic field strength parallel to the detection surface 40 is small in the region above the hole in the pole piece 74, and the value of the parallel component of the magnetic field is significantly less than that illustrated in the prior art cases shown in FIGS. 2 and 3.

FIG. 8 (C) is a perspective view of the pole piece 64 described in Example 3, wherein the holes 72 can be realized by casting, stamping, cutting and other methods.

Example 4

Figure 9:
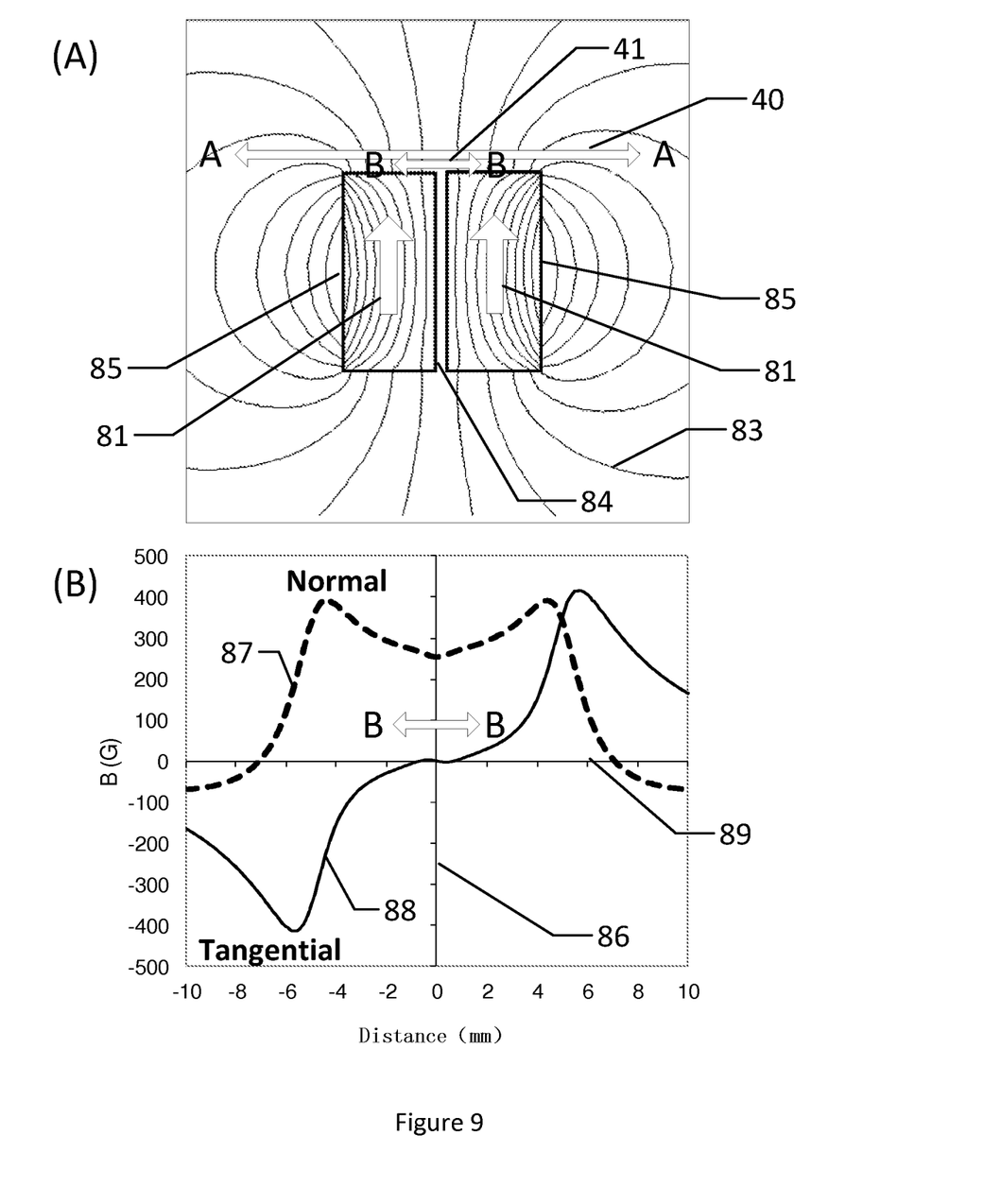

FIG. 9 (A) to the magnetic field lines of the magnetic field distribution in the magnetic head of Example 4 produced by the bias unit. In this design, there is a spacer layer 84 between the two rectangular permanent magnets 85, and the material for the spacer layer 84 may be a non-magnetic metallic material, a plastic non-magnetic material, a non-magnetic ceramic material, or a soft ferromagnetic material such as iron. The magnetization direction of the permanent magnets 85 is perpendicular to the detection surface 40. In the region above the spacer layer 84, the component of the magnetic field parallel to the detection surface 40 is zero.

FIG. 9 (B) shows the magnetic field distribution along the sensing surface 40 in the figure, wherein the dashed line 87 is the vertical component of the magnetic field on the detection surface 40, the thin solid line 88 is the parallel component of the magnetic field on detection surface 40, the vertical axis 86 is magnetic induction, and the horizontal axis is the distance from the center of the detection surface 40. As can be seen from the figure, the magnetic field strength parallel to the detection surface 40 is small in the region above the spacer layer 84, and the value of the parallel component of the magnetic field is significantly less than that illustrated in the prior art cases shown in FIGS. 2 and 3.

The implementation is not limited in scope to the specific examples cited above. For those skilled in the art, the present subject matter may be accomplished through various changes in and variations of the specific examples. Any modification within the spirit and principles of the present subject matter described herein is considered within the scope of the present invention.

The invention claimed is:

1. A magnetic currency verification head comprising:
    a magnetoresistive sensor chip and a separate magnetic bias unit disposed on the side of the magnetoresistive sensor chip away from the magnetic currency verification head detection surface,
    the magnetoresistive sensor chip comprising a gradiometric bridge circuit that includes magnetic sensor elements with a sensitive direction parallel to a magnetic currency verification head detection surface; and
    the magnetic bias unit configured to generate a small magnetic bias field in the direction parallel to the magnetic currency verification head detection surface to enable the magnetic sensor elements to operate in their linear range, wherein the magnetic bias unit includes a magnetic bias configuration selected from the group of magnetic bias configurations consisting of:
        a first magnetic bias configuration that includes:
            a rectangular permanent magnet having a side facing the magnetoresistive sensor chip with a magnetic surface parallel to the magnetic currency verification head detection surface, and
            a pole piece composed of high permeability magnetic material on the magnetic surface, wherein the pole piece surface has a recessed rectangular cavity;
        a second magnetic bias configuration that includes:
            a rectangular permanent magnet having a side facing the magnetoresistive sensor chip with a magnetic surface parallel to the magnetic currency verification head detection surface, and
            a rectangular-ring-shaped pole-piece composed of high permeability magnetic material on the rectangular permanent magnet; and
        a third magnetic bias configuration that includes:
            two separately disposed rectangular permanent magnets, each having a side facing the magnetoresistive sensor chip with a magnetic surface parallel to the magnetic currency verification head detection surface, and
            a non-magnetic material or a soft ferromagnetic material between the rectangular permanent magnets.

2. The magnetic currency verification head of claim 1 wherein the magnetic field generated by the magnetic bias unit in a direction parallel to the sensing direction of the magnetic sensor elements is less than 25 gauss.

3. The magnetic currency verification head of claim 1 wherein the magnetic sensor elements are tunneling magnetoresistive (TMR) elements, giant magnetoresistive (GMR) elements, or anisotropic magnetoresistive (AMR) elements.

4. The magnetic currency verification head of claim 3 wherein the TMR, GMR, or AMR magnetic sensor elements are connected in series, parallel, or a combination of series and parallel.

5. The magnetic currency verification head of claim 1 further comprising a metal casing to enclose the magnetoresistive sensor chip and the magnetic bias unit, wherein the metal casing has an opening on the side opposite to the magnetic currency verification head detection surface.

6. The magnetic currency verification head of claim 1 further comprising a metal casing to enclose the magnetoresistive sensor chip and the magnetic bias unit, wherein the metal casing is provided with a ground terminal.

7. The magnetic currency verification head of claim 5 wherein the metal casing is filled with injection molded material to secure the components.

8. The magnetic currency verification head of claim 6 wherein the metal casing is filled with injection molded material to secure the components.

9. A magnetic currency verification head, comprising:
    a magnetic currency verification head detection surface;
    a magnetic bias unit comprising a permanent magnet having a magnetic surface parallel to the magnetic currency verification head detection surface, and a pole piece composed of high permeability magnetic material on the magnet surface; and
    a magnetoresistive sensor chip between the magnetic bias unit and the magnetic currency verification head detection surface, the magnetoresistive sensor chip including a gradiometric bridge circuit with bridge arms, the bridge arms including magnetic sensor elements with a sensitive direction parallel to a magnetic currency verification head detection surface, wherein the magnetic sensor elements are selected from a group of sensor elements consisting of: tunneling magnetoresistive (TMR) elements, giant magnetoresistive (GMR) elements, or anisotropic magnetoresistive (AMR) elements, wherein the pole piece is configured with a shape to cause the magnetic bias unit to generate a small magnetic bias field in the direction parallel to the magnetic currency verification head detection surface, thereby enabling the magnetic sensor elements to operate in their linear range.

10. The magnetic currency verification head of claim 9 wherein the pole-piece includes a recessed rectangular cavity.

11. The magnetic currency verification head of claim 9 wherein the pole-piece includes a rectangular-ring-shaped pole piece.

12. The magnetic currency verification head of claim 9 further comprising a metal casing to enclose the magnetoresistive sensor chip and the magnetic bias unit, wherein the metal casing has an opening on the side opposite to the magnetic currency verification head detection surface.

13. The magnetic currency verification head of claim 9 wherein the small magnetic field generated by the magnetic bias unit in a direction parallel to the sensing direction of the magnetic sensor elements is less than 25 gauss.

14. A magnetic currency verification head, comprising:
a magnetic currency verification head detection surface;
a magnetic bias unit; and
a magnetoresistive sensor chip between the magnetic bias unit and the magnetic currency verification head detection surface, the magnetoresistive sensor chip including a gradiometric bridge circuit with bridge arms, the bridge arms including magnetic sensor elements with a sensitive direction parallel to a magnetic currency verification head detection surface, wherein the magnetic sensor elements are selected from a group of sensor elements consisting of: tunneling magnetoresistive (TMR) elements, giant magnetoresistive (GMR) elements, or anisotropic magnetoresistive (AMR) elements, wherein the magnetic bias unit includes two separately disposed rectangular permanent magnets, each having a side facing the magnetoresistive sensor chip with a magnetic surface parallel to the magnetic currency verification head detection surface, and a non-magnetic material or a soft ferromagnetic material between the rectangular permanent magnets to cause the magnetic bias unit to generate a small magnetic bias field in the direction parallel to the magnetic currency verification head detection surface, thereby enabling the magnetic sensor elements to operate in their linear range.

15. The magnetic currency verification head of claim 14 wherein the small magnetic field generated by the magnetic bias unit in a direction parallel to the sensing direction of the magnetic sensor elements is less than 25 gauss.

* * * * *